United States Patent
Roussel

(10) Patent No.: US 8,201,466 B2
(45) Date of Patent: Jun. 19, 2012

(54) MULTI-CHANNEL PIPETTE INCLUDING A PISTON HOLDER WITH GUIDANCE

(75) Inventor: Bernard Roussel, Bondy (FR)

(73) Assignee: Gilson S. A. S., Villiers-le-Bel (FR)

(*) Notice: Subject to any disclaimer, the term of this patent is extended or adjusted under 35 U.S.C. 154(b) by 690 days.

(21) Appl. No.: 12/206,472

(22) Filed: Sep. 8, 2008

(65) Prior Publication Data

US 2009/0064801 A1    Mar. 12, 2009

(30) Foreign Application Priority Data

Sep. 10, 2007   (FR) ...................................... 07 57448

(51) Int. Cl.
*B01L 3/02* (2006.01)
*G01N 1/14* (2006.01)
(52) U.S. Cl. .................................. 73/863.32; 73/864.17
(58) Field of Classification Search ............... 73/863.32, 73/864.17, 864.13
See application file for complete search history.

(56) References Cited

U.S. PATENT DOCUMENTS

| | | | |
|---|---|---|---|
| 5,273,717 A | | 12/1993 | Marvin |
| 6,199,435 B1* | | 3/2001 | Wilmer et al. ............. 73/864.14 |
| 7,146,867 B2* | | 12/2006 | Jagdhuber .................. 73/863.32 |
| 7,943,393 B2* | | 5/2011 | Gjerde et al. .......... 73/864.17 X |
| 2001/0039843 A1* | | 11/2001 | Schoeppe ................. 73/863.32 |
| 2001/0043885 A1* | | 11/2001 | Wanner .................. 73/863.32 X |
| 2004/0026444 A1* | | 2/2004 | DeSilva et al. ........ 73/863.32 X |
| 2004/0050866 A1 | | 3/2004 | Ingenhoven et al. |
| 2004/0076550 A1 | | 4/2004 | Ruedisser et al. |
| 2004/0149052 A1 | | 8/2004 | Jagdhuber |
| 2004/0226389 A1* | | 11/2004 | Thom et al. ................ 73/864.17 |
| 2006/0144169 A1* | | 7/2006 | Porat et al. ............. 73/863.32 X |

(Continued)

FOREIGN PATENT DOCUMENTS

DE    10 2007 01848    10/2007

(Continued)

OTHER PUBLICATIONS

Gilson, "Pipetman Neo User's Guide" [Online]Jan. 2009, pp. 1-32, XP002552040 Retrieved from the Internet:URL:http://gilson.com/Resources/LT801521_a_eng_30209%20bd.pdf> The printed date is Jan. 2009 and the publication date is Mar. 4, 2009.

(Continued)

*Primary Examiner* — Thomas P Noland
(74) *Attorney, Agent, or Firm* — Foley & Lardner LLP

(57) ABSTRACT

A device for use in a multi-channel pipetting system is provided. The device includes a body, a plurality of modules mounted to the body, a plurality of pistons mounted to a piston holder for simultaneous movement of the plurality of pistons in a first direction, and a guidance assembly. Each module includes an orifice connecting to an intake chamber. A piston extends into the intake chamber for movement in the first direction. The guidance assembly includes a first rotating element, a second rotating element, a shaft connecting the first rotating element to the second rotating element, and a first track and a second track extending parallel to the first direction. The shaft extends in a second direction orthogonal to the first direction. The first rotating element is mounted to roll along the first track, and the second rotating element is mounted to roll along the second track simultaneously with the plurality of pistons.

20 Claims, 8 Drawing Sheets

U.S. PATENT DOCUMENTS

2007/0081155 A1* 4/2007 Schembri et al. ...... 73/863.32 X
2007/0297948 A1 12/2007 May et al.

FOREIGN PATENT DOCUMENTS

| EP | 0 046 461 | | 3/1982 |
|----|-----------|---|--------|
| EP | 1 439 002 | | 7/2004 |
| EP | 1 679 122 | | 7/2006 |
| FR | 1 411 283 | | 9/1965 |
| GB | 2 045 641 | | 11/1980 |
| JP | 55131770 A | * | 10/1980 |
| WO | WO 02/16036 | | 2/2002 |
| WO | WO 2006/087444 | | 8/2006 |
| WO | WO 2009/034435 | | 3/2009 |

OTHER PUBLICATIONS

International Search Report and Written Opinion for PCT/IB2009/005010 mailed Nov. 3, 2009.
International Preliminary Report on Patentability for PCT/IB2008/002325 mailed Mar. 25, 2010.
International Search Report and Written Opinion for PCT/IB2008/002325 mailed Feb. 19, 2009.
French Search Report for FR 07 57448 dated Apr. 16, 2008.
International Preliminary Report on Patentability issued in PCT/IB2009/005010 and mailed Jul. 28, 2011.
Office Action issued in Chinese Patent Application No. 200880106259.7 and dated Mar. 1, 2012.

* cited by examiner

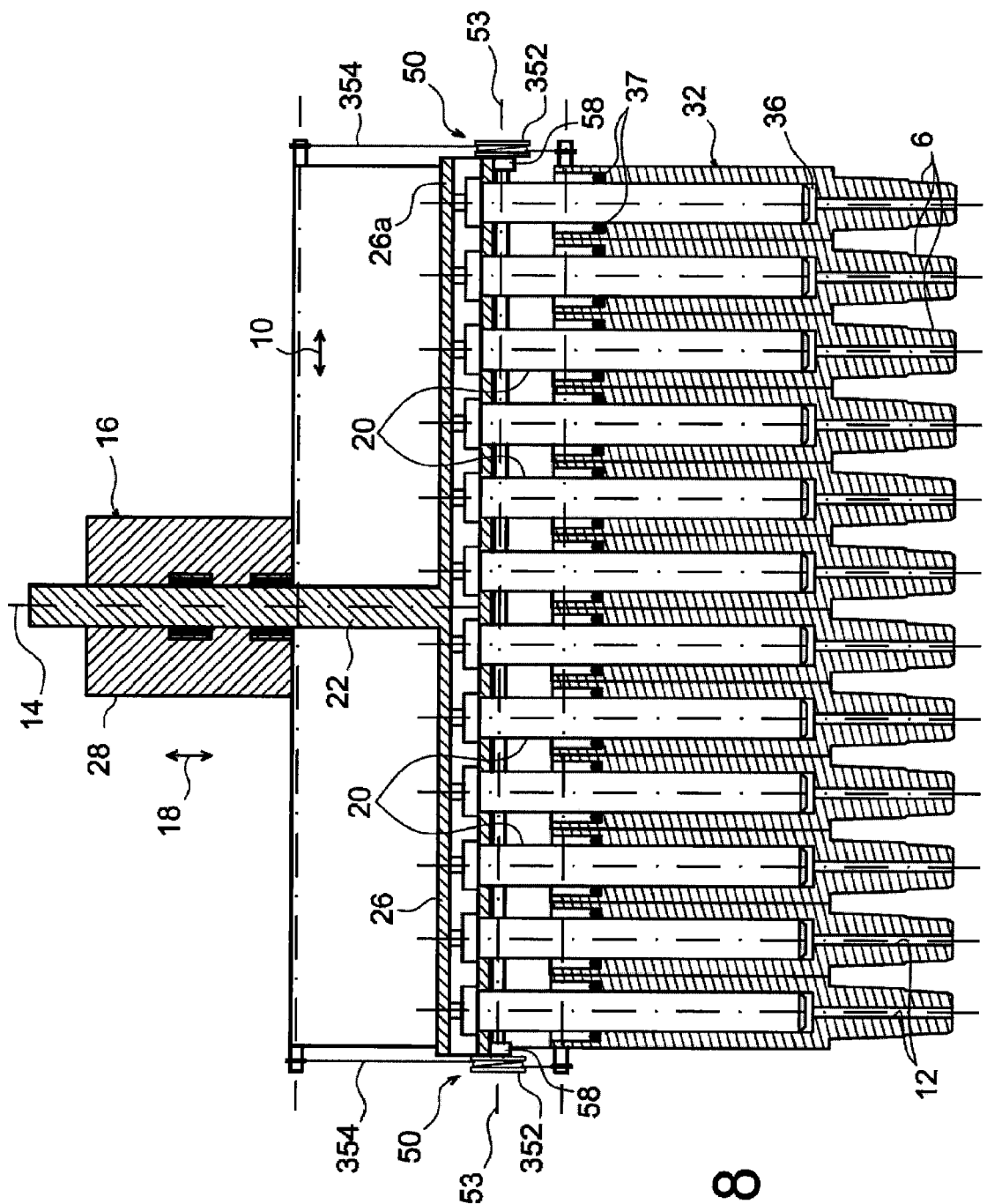

MULTI-CHANNEL PIPETTE INCLUDING A PISTON HOLDER WITH GUIDANCE

CROSS-REFERENCE TO RELATED APPLICATIONS

This application claims priority under the Paris Convention to French Patent Application No. 0757448, filed Sep. 10, 2007, the disclosure of which is incorporated by reference in its entirety.

BACKGROUND

Multi-channel pipetting systems include a multi-channel sampling pipette intended for the calibrated aspiration of liquids and the subsequent deposition of the liquids into receptacles. Sampling pipettes can be held in the hand of an operator during aspiration and dispensation of the liquid or may be included as part of an automated system. As an example, a multi-channel pipette may include a body forming a handle, in addition to a bottom part which, at its end, includes a plurality of pipette sampling tubes on which sampling cones can be positioned. The bottom part includes a fixed body which, at its bottom end, has a plurality of sampling tubes spaced from each other in a sideways direction relative to the pipette body, with each sampling tube including an orifice communicating with an intake chamber.

Parallel pistons are positioned in the intake chambers, and mounted at their upper ends to a piston holder that can be translated relative to the fixed body. The piston holder may be controlled by a manual or a motor-driven arrangement that causes the piston holder to rise during the liquid sampling or aspiration phase and causes the piston holder to descend during the liquid transfer phase, with the upward motion achieved, in general, by the expansion of a spring that was compressed during the downward movement.

During its movement, the piston holder carries with it the pistons that are attached to it so that the pistons are capable of simultaneous motion in a sliding movement that is usually parallel to a longitudinal central axis of the pipette. As an example, upward motion imposed on the piston holder, and therefore on the pistons, determines the volume of liquid drawn up. The volume is selected beforehand by the user, for example, using a control knob, an adjusting screw, a digital keypad, etc.

The piston holder usually includes a guide rod parallel to a longitudinal central axis of the pipette, mounted to slide on the fixed body by means of two bearings spaced along the longitudinal central axis. The piston holder additionally includes a piston support head attached to the bottom end of the rod and accommodating the top end of the pistons. In this case, the piston support head is arranged parallel to the lateral direction, and therefore orthogonal to a longitudinal central axis of the pipette.

The precision and accuracy of the volume aspirated depends on the ability to reproduce, for each piston, the same simultaneous distance of travel for a given volume setting. However, it has been observed that during the use of a multi-channel pipette, the support head of the piston holder, also known as the "rake", has a tendency to move without maintaining orthogonality with the sliding direction resulting in a slightly inclined plane determined by the lateral direction and the sliding direction. This effect, known as the "rake effect," occurs during the reciprocating motion of the piston holder and results in a difference in the distance of travel for one piston relative to another piston thereby reducing the precision and accuracy of the volume aspirated between the plurality of pistons. The rake effect may be caused by a large amount of play between the guide rod and the guide bearings, by an unsuitable shape of the return spring that is used to raise the piston holder, by inadequate stiffness of the piston holder, by an imbalance in the friction of the sealing gaskets mating with the pistons, etc.

SUMMARY

In an exemplary embodiment, a device for use in a multi-channel pipetting system is provided. The device includes, but is not limited to, a body, a plurality of modules mounted to the body, a plurality of pistons mounted to a piston holder for simultaneous movement of the plurality of pistons in a first direction, and a guidance assembly. Each module of the plurality of modules includes, but is not limited to, an orifice connecting to an intake chamber. A piston of the plurality of pistons extends into the intake chamber of a module of the plurality of modules for movement in the first direction. The guidance assembly includes, but is not limited to, a first rotating element, a second rotating element, a shaft connecting the first rotating element to the second rotating element, and a first track and a second track extending parallel to the first direction. The shaft extends in a second direction orthogonal to the first direction. The first rotating element is mounted to roll along the first track, and the second rotating element is mounted to roll along the second track simultaneously with the plurality of pistons.

In another exemplary embodiment, a multi-channel pipetting system is provided. The multi-channel pipetting system includes, but is not limited to, a first part, and a second part. The first part is configured to control movement of a guide rod when the second part is mounted to the first part. The second part includes, but is not limited to a body, a plurality of modules mounted to the body, a piston support head mounted to the guide rod, a plurality of pistons mounted to the piston support head for simultaneous movement of the plurality of pistons in a first direction, and a guidance assembly. Each module of the plurality of modules includes, but is not limited to, an orifice connecting to an intake chamber. A piston of the plurality of pistons extends into the intake chamber of a module of the plurality of modules for movement in the first direction. The guidance assembly includes, but is not limited to, a first rotating element, a second rotating element, a shaft connecting the first rotating element to the second rotating element, and a first track and a second track extending parallel to the first direction. The shaft extends in a second direction orthogonal to the first direction. The first rotating element is mounted to roll along the first track, and the second rotating element is mounted to roll along the second track simultaneously with the plurality of pistons.

Other principal features and advantages of the invention will become apparent to those skilled in the art upon review of the following drawings, the detailed description, and the appended claims.

BRIEF DESCRIPTION OF THE DRAWINGS

Exemplary embodiments of the invention will hereafter be described with reference to the accompanying drawings, wherein like numerals denote like elements.

FIG. 8 shows a front, cross sectional view of the second bottom part of FIG. 7 in accordance with an exemplary embodiment.

DETAILED DESCRIPTION

Figure 1:
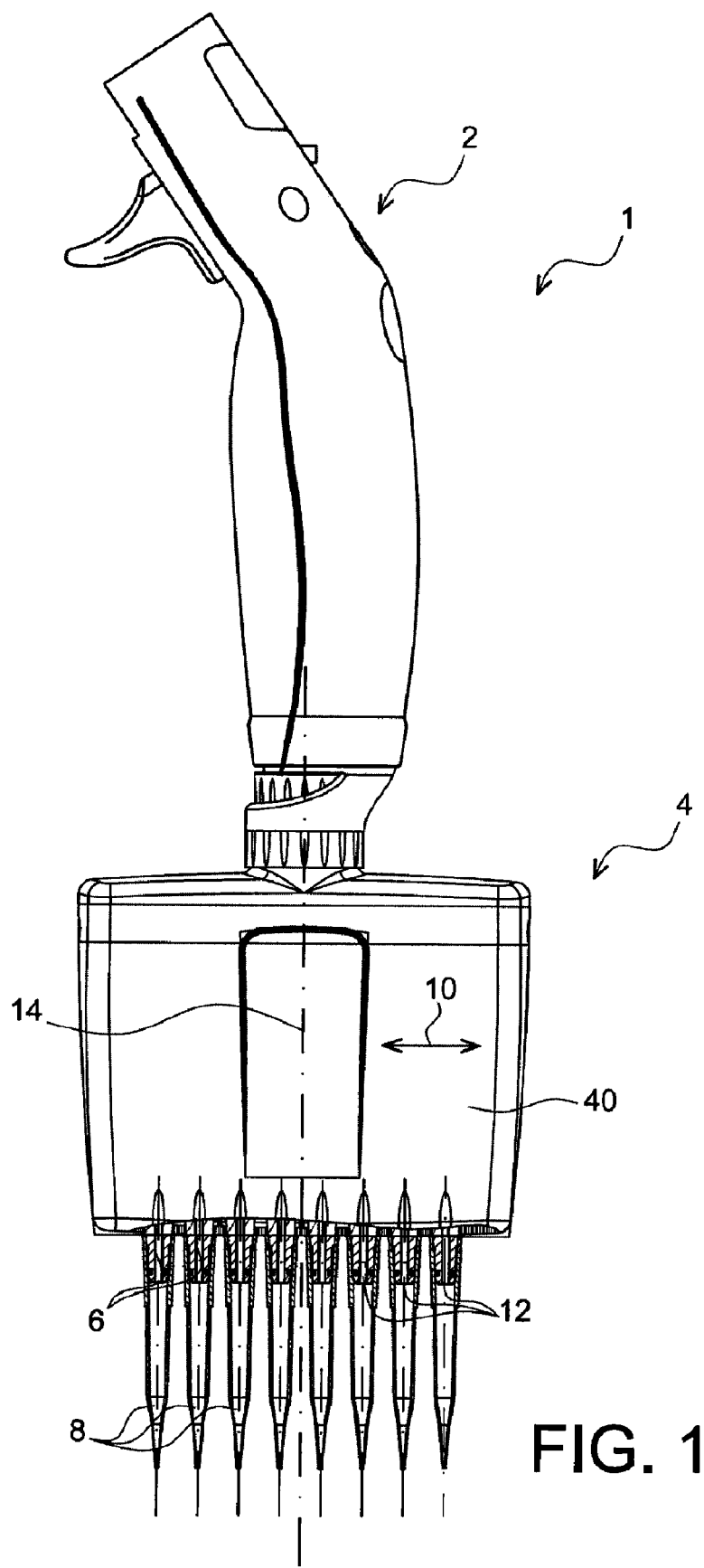
FIG. 1 shows a side view of a multi-channel pipette in accordance with an exemplary embodiment.

With reference to FIG. 1, a side view of a multi-channel pipette 1 is shown in accordance with an exemplary embodiment. In other exemplary embodiments, any multi-channel pipetting system may be used. Multi-channel pipette 1 may be manually driven or motor driven. Multi-channel pipette 1 may include a top part including a body forming a handle 2 and a bottom part 4. At its bottom end, bottom part 4 includes pipette sampling cone-carrying adapters 6 and a removable cover 40. Sampling cones can be press fit onto the pipette sampling cone-carrying adapters 6.

The sampling, cone-carrying adapters 6 are spaced from each other in a sideways direction of multi-channel pipette 1, or in a lateral pipette direction, represented by a lateral direction 10, with each adapter 6 having an orifice 12 communicating at its top end with an intake chamber (not shown in FIG. 1), and at its bottom end with a sampling cone 8.

Multi-channel pipette 1 has a longitudinal central axis 14 that also corresponds to a longitudinal central axis of the bottom part 4. Longitudinal central axis 14 is orthogonal to lateral direction 10, and may be placed to have an identical number of adapters 6 positioned on either side of longitudinal central axis 14 in the lateral direction. In general, longitudinal central axis 14 is parallel to the axes of the orifices 12 and their associated sampling cones 8 and to the sliding direction of the mobile elements of bottom part 4. Bottom part 4 may be removed from and mounted to handle 2, for example by screwing the bottom part 4 onto handle 2. As used herein, the term "mount" includes join, unite, connect, associate, insert, hang, hold, affix, attach, fasten, bind, paste, secure, bolt, screw, rivet, solder, weld, press against, and other like terms.

Figure 2:
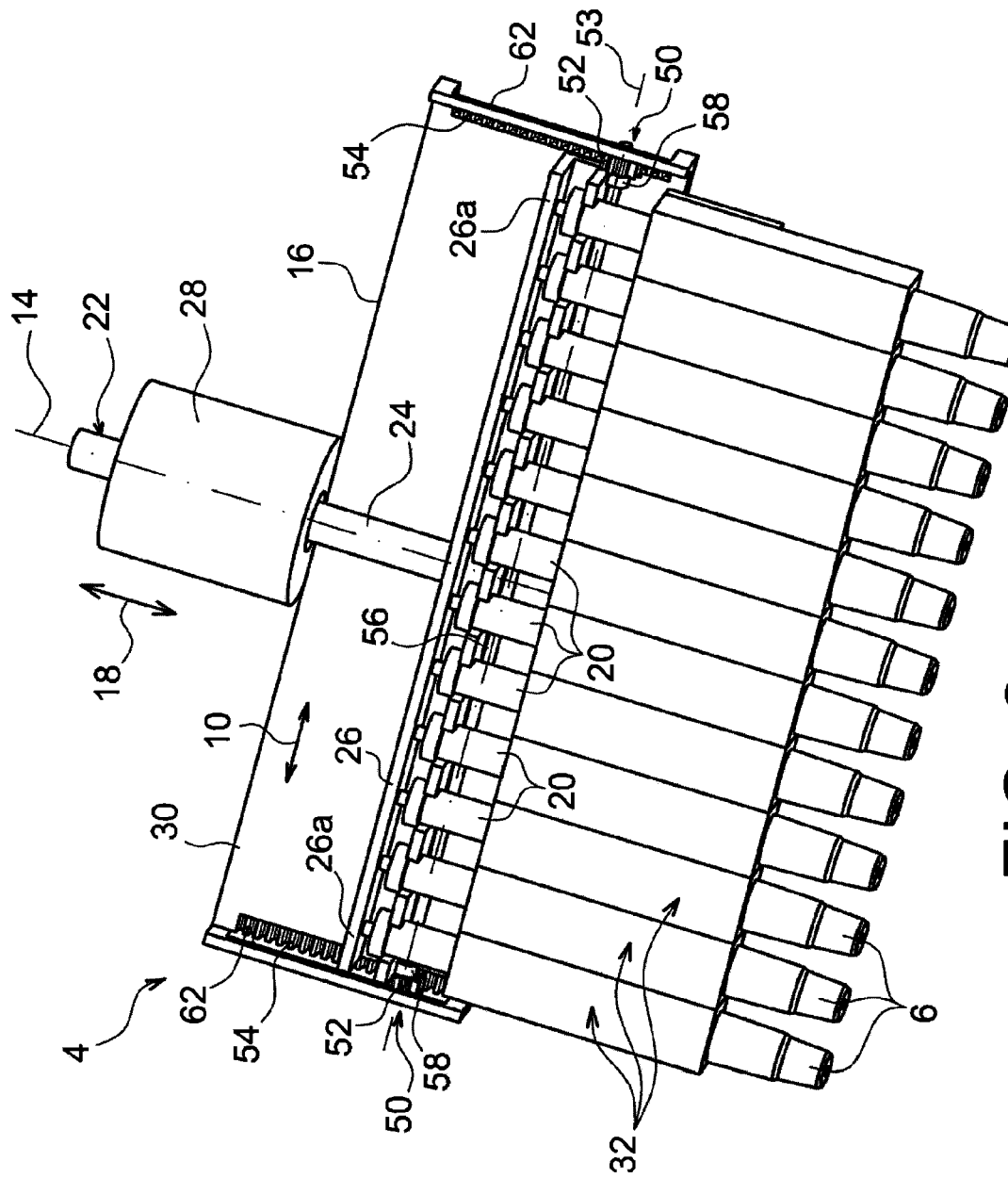
FIG. 2 shows a front, perspective view of a bottom part of the multi-channel pipette of FIG. 1 in accordance with an exemplary embodiment.
Figure 3:
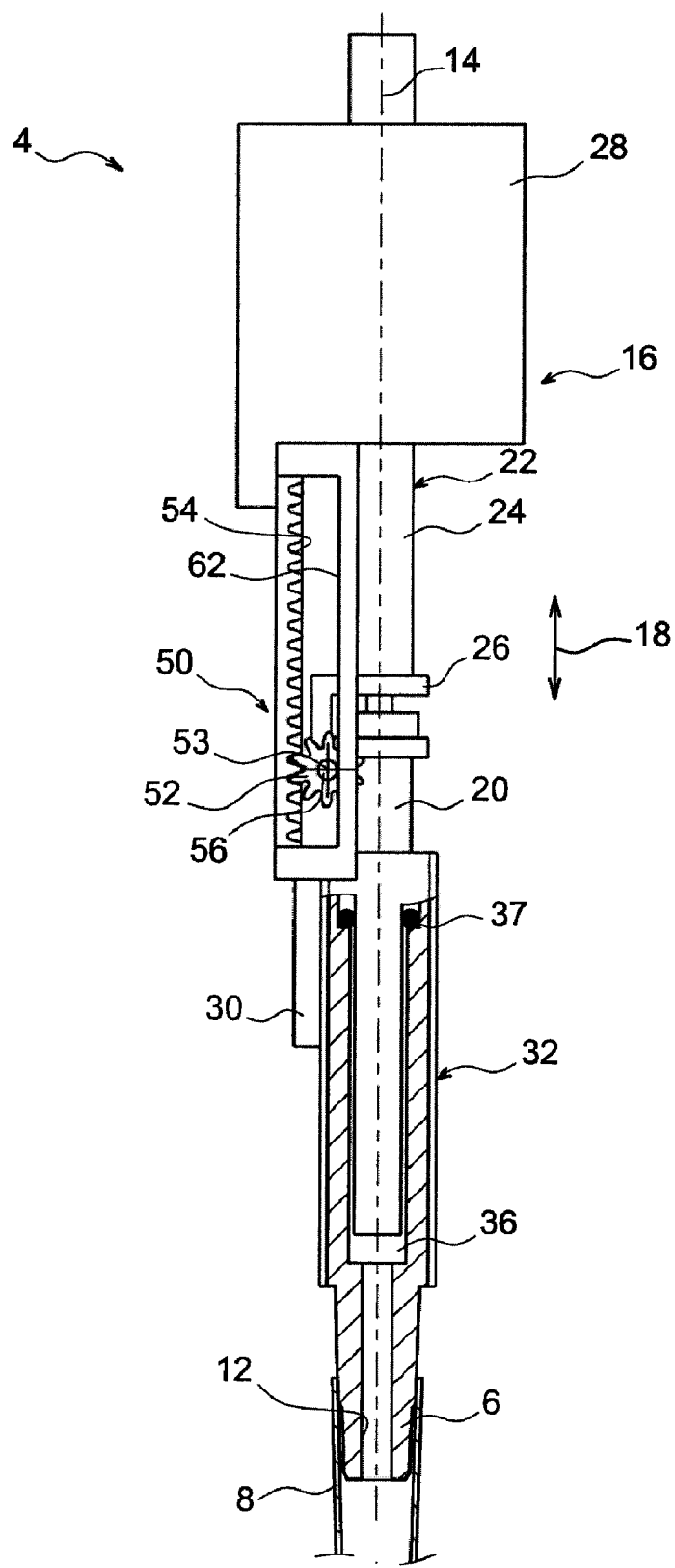
FIG. 3 shows a side view of a first guidance assembly of a piston block assembly of the bottom part of FIG. 2 in accordance with an exemplary embodiment.

With reference to FIGS. 2 and 3, a front, perspective view of bottom part 4 of multi-channel pipette 1 is shown in accordance with an exemplary embodiment. Bottom part 4 includes a fixed body 16 and an assembly that is mobile in relation to fixed body 16 in a sliding movement direction 18 parallel to longitudinal central axis 14 and orthogonal to lateral direction 10. The mobile assembly has a plurality of pistons 20 mounted parallel to sliding movement direction 18 and spaced from each other in lateral direction 10. In an exemplary embodiment, the plurality of pistons 20 are mounted in a single plane. Each of the plurality of pistons 20 is associated with an adapter of the sampling, cone-carrying adapters 6.

The mobile assembly also may include a piston holder 22 and a piston support head 26. Piston holder 22 is located generally above the plurality of pistons 20 and may include a guide rod 24 centered on longitudinal central axis 14. Piston support head 26 is mounted to the bottom end of guide rod 24. Piston support head 26 is mounted parallel to lateral direction 10 and orthogonal to sliding movement direction 18 and to longitudinal central axis 14. Piston support head 26 has the form of a rake accommodating the top end of the plurality of pistons 20 between its teeth. Each top end of a piston of the plurality of pistons 20 is locked in translation by the rake in both directions of sliding movement direction 18 to follow the reciprocating motion of piston holder 22 in sliding movement direction 18.

Fixed body 16 of bottom part 4 is formed of several elements mounted together or made as a unit. Fixed body 16 may include a guidance cylinder 28 centered on longitudinal central axis 14 to accommodate the sliding action of guide rod 24. A support structure 30 is mounted below guidance cylinder 28 and forms a sliding space for piston support head 26. In an exemplary embodiment, support structure 30 is substantially oriented in a plane parallel to lateral direction 10 and sliding movement direction 18. A bottom end of support structure 30 acts as a support for individual, firmly associated modules 32. The modules 32 form the sampling, cone-carrying adapters 6 at a lower end. In another exemplary embodiment, the modules 32 may be formed of a single part.

With reference to FIG. 3, each module 32, together with its top portion, forms an intake chamber 36 accommodating the sliding action of a piston of the plurality of pistons 20, with sealing provided, for example, by placing an o-ring 37 in a seam in the intake chamber 36. The bottom part is used to create the adapter 6 and its orifice 12 with the top end of orifice 12 communicating with the bottom of the intake chamber 36. Removable cover 40 generally covers support structure 30 and the modules 32 so that only a bottom part of the sampling, cone-carrying adapters 6 project outside removable cover 40.

Guide rod 24 of piston holder 22 is driven by a manual or motor-driven arrangement that causes guide rod 24 to rise during the liquid sampling phase and to descend during the liquid transfer phase with the upward motion achieved, for example, by the expansion of a spring that was compressed during the previous downward movement. During its movement, piston holder 22 carries the plurality of pistons 20 attached to piston support head 26 so that the plurality of pistons 20 are moved simultaneously in the sliding movement direction 18. The upward motion imposed upon the mobile assembly in relation to fixed body 16 determines the volume of liquid aspirated.

With continuing reference to FIGS. 2 and 3, piston holder 22 includes a guidance assembly 50. In an exemplary embodiment, guidance assembly 50 includes a plurality of rotating elements and a track associated with each of the plurality of rotating elements. In the exemplary embodiment of FIGS. 2 and 3, guidance assembly 50 includes a toothed wheel 52 and a rack 54. In the exemplary embodiment, guidance assembly 50 includes two lateral rotating elements spaced along lateral direction 10 on either side of longitudinal central axis 14 at two lateral ends of piston holder 22. Guidance assembly 50 is provided to eliminate or reduce the rake effect during the reciprocating movement of piston holder 22 by applying to the two lateral ends 26a of piston support head 26 an identical and simultaneous movement relative to fixed body 16.

In the exemplary embodiment of FIGS. 2 and 3, toothed wheel 52 is mounted to rotate freely on an axis of rotation 53 orthogonal to the sliding movement direction 18 and parallel to lateral direction 10 on one end of piston support head 26.

rack 54 is mounted on fixed body 16, for example, on support structure 30, with rack 54 mounted parallel to sliding movement direction 18. For example, rack 54 can be created in the thickness of support structure 30 in sheet form. Guidance assembly 50 is mounted so that each toothed wheel 52 runs without slipping along its corresponding rack 54 by virtue of a geared connection.

The toothed wheels 52 are mounted on the same axis of rotation 53 and are connected firmly together by a connecting shaft 56 arranged on axis of rotation 53. In an exemplary embodiment, connecting shaft 56 is fitted to rotate freely on axis of rotation 53 on piston support head 26 of piston holder 22 by means of rings 58 carried by the lateral ends 26a of piston support head 26. Thus, the guidance assembly 50 that includes the toothed wheels 52 and the connecting shaft 56 is capable of rotating about axis of rotation 53 in relation to piston support head 26 and remains locked in translation with piston support head 26 in sliding movement direction 18. By virtue of the presence of connecting shaft 56, the toothed wheels 52 are locked to each other in rotation on axis of rotation 53 so that during a movement of piston holder 22 in sliding movement direction 18, the toothed wheels 52 move simultaneously by the same distance along their respective rack 54 to apply identical movement to the two lateral ends 26a of piston support head 26, due to the coupling in rotation of toothed wheels 52 and to the slip-free connection to the respective rack 54. When one of the toothed wheels 52 is put into rotation due to the movement in translation of piston holder 22 in sliding movement direction 18, the other toothed wheel 52 is simultaneously put into rotation with the same amplitude because of their coupling in rotation so that both toothed wheels 52 move the same distance along their respective rack 54, therefore resulting in a precise and controlled movement of piston support head 26. The plurality of rotating elements jointly guarantee a balancing of all of the plurality of pistons 20 of piston holder 22 during the reciprocating movement in sliding movement direction 18, enabling piston holder 22 to maintain its normal position in which piston support head 26 is parallel to lateral direction 10 and orthogonal to sliding movement direction 18.

To ensure a good fit between each toothed wheel 52 and its corresponding rack 54, each of the two ends of connecting shaft 56 are arranged to be continuously in contact with a contact track 62 provided on fixed body 16, for example, on support structure 30. Contact track 62 can be of the longitudinal groove type extending parallel to longitudinal central axis 14 with a contact surface that receives the end of connecting shaft 56, oriented toward the rack 54 to ensure pressing of toothed wheel 52 onto rack 54.

In an alternative embodiment, rack 54 can be replaced by a chain that mates with toothed wheel 52. The chain may be tensioned by securing its two ends to fixed body 16, for example, to support structure 30.

Figure 4:
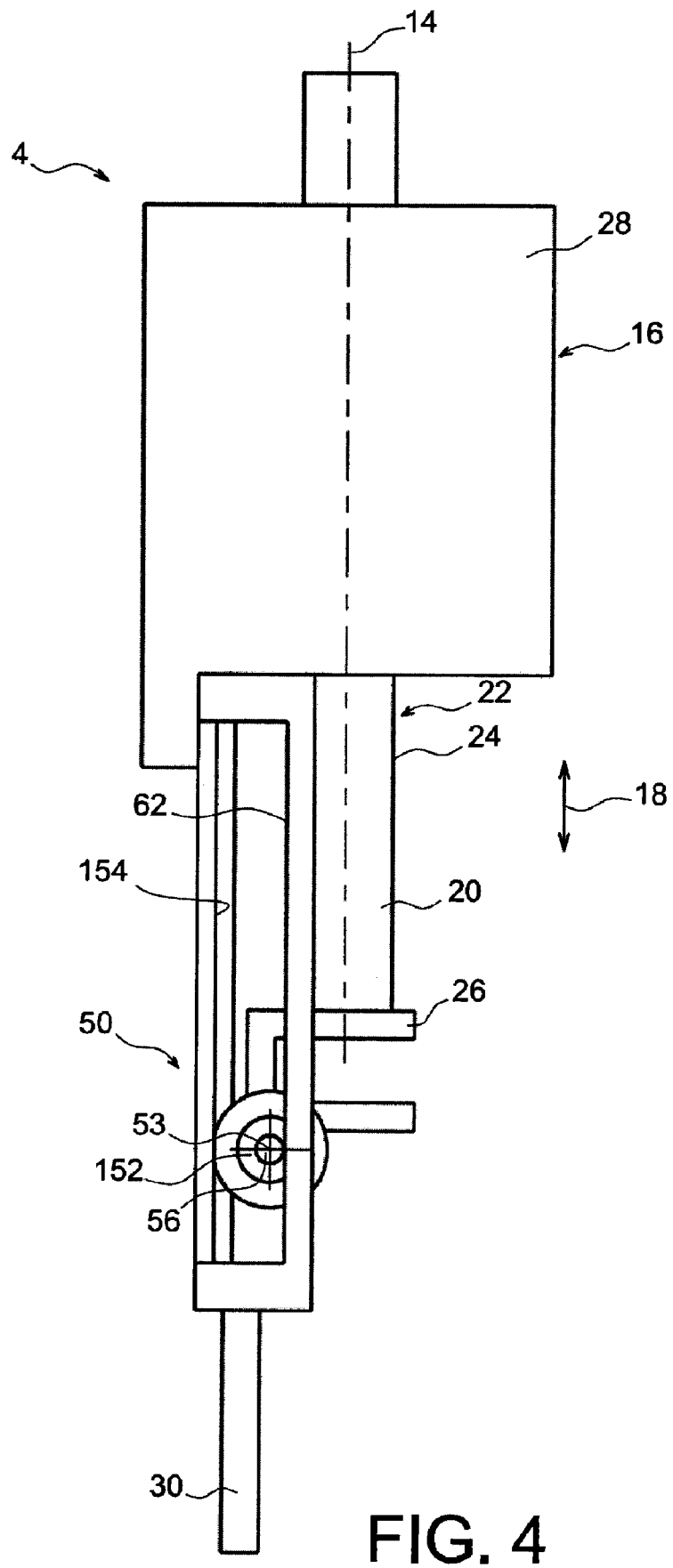
FIG. 4 shows a side view of a second guidance assembly of the multi-channel pipette of FIG. 1 in accordance with an exemplary embodiment.
Figure 5:
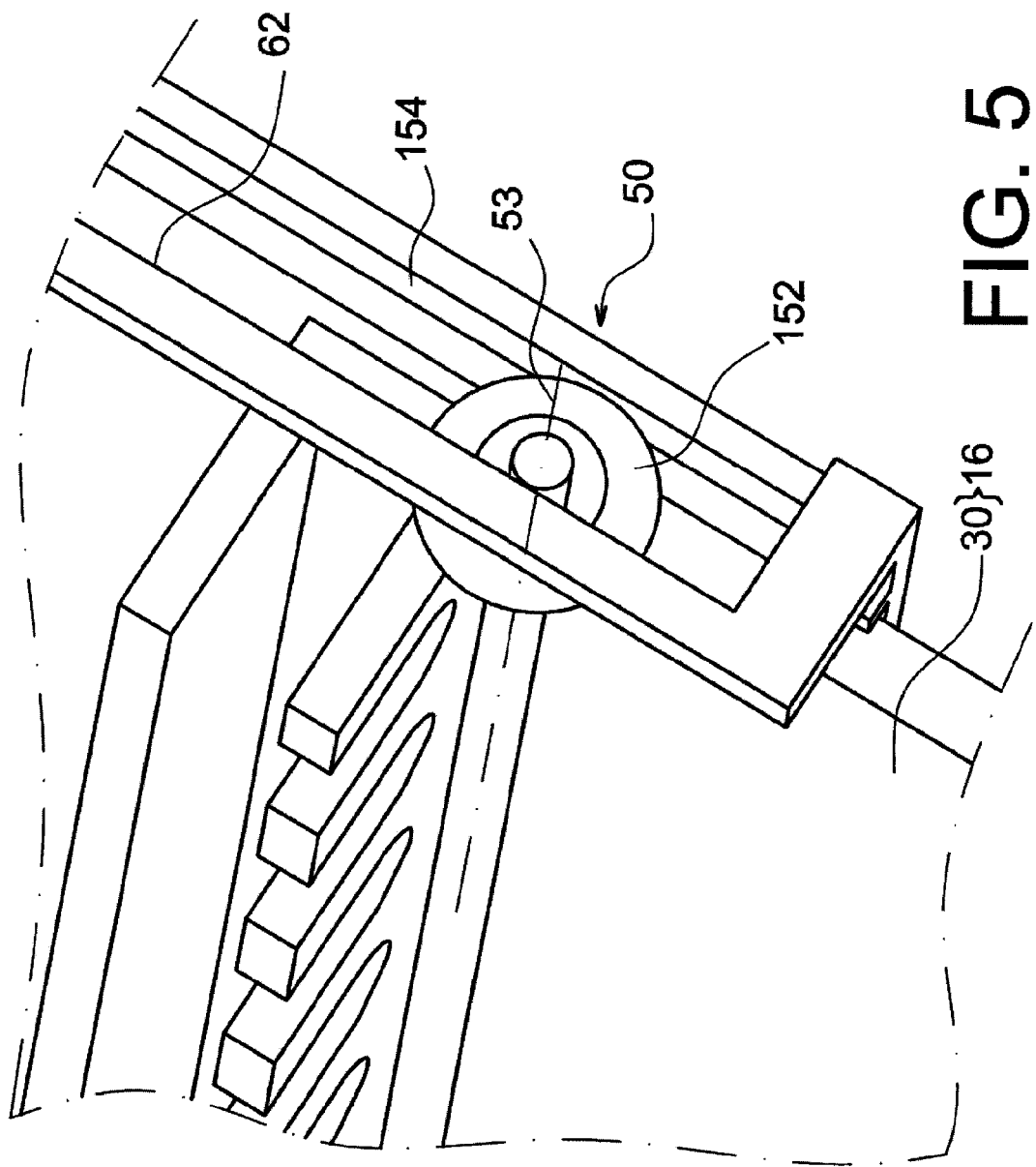
FIG. 5 shows a close-up, front, perspective view of the second guidance assembly of FIG. 4 in accordance with an exemplary embodiment.

With reference to FIGS. 4 and 5, a second guidance assembly 50 of the multi-channel pipette of FIG. 1 is shown in accordance with an exemplary embodiment. The second guidance assembly 50 includes a pulley 152 as the rotating element replacing each toothed wheel 52. The pulley 152 on the axis of rotation 53 mates with a track formed by a smooth surface 154 extending parallel to sliding movement direction 18. The pulley 152 may be formed, for example, with a periphery in an elastomer material and with the slip-free connection on smooth surface 154 being provided by being pressed onto the same surface by virtue of contact track 62 in continuous contact with the end of connecting shaft 56.

Figure 6:
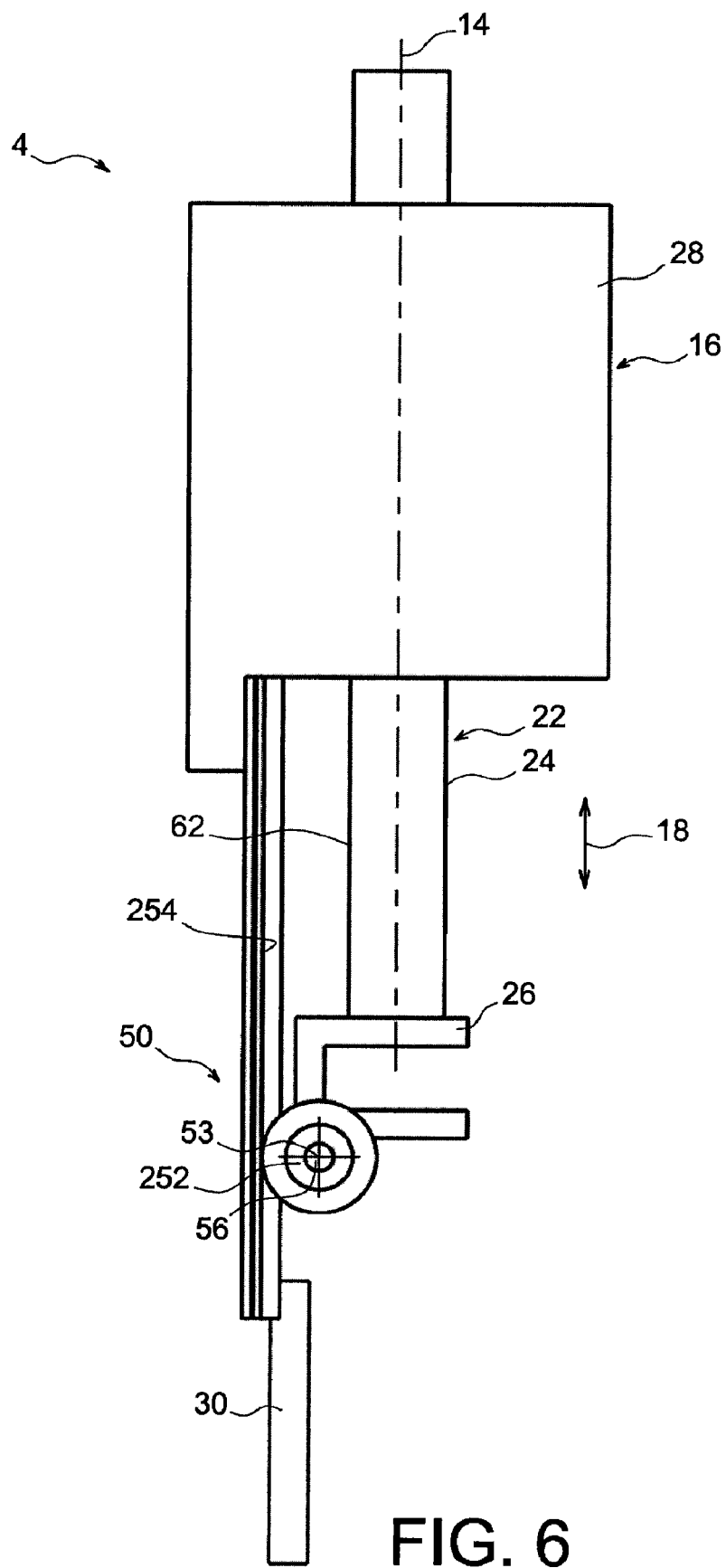
FIG. 6 shows a side view of a third guidance assembly of the multi-channel pipette of FIG. 1 in accordance with an exemplary embodiment.

With reference to FIG. 6, a third guidance assembly 50 of the multi-channel pipette of FIG. 1 is shown in accordance with an exemplary embodiment. The third guidance assembly 50 includes a second pulley 252 on the axis of rotation 53 and carried by the connecting shaft 56. The material of second pulley 252 is selected to create a magnetic attraction to a track formed by a surface 254. The continuous force of magnetic attraction between the surface 254 and the second pulley 252 results in a slip-free operation such that the ends of connecting shaft 56 no longer need to fit onto contact track 62. Thus, the design of bottom part 4 is simplified by eliminating the contact track 62 in the form of grooves.

Figure 7:
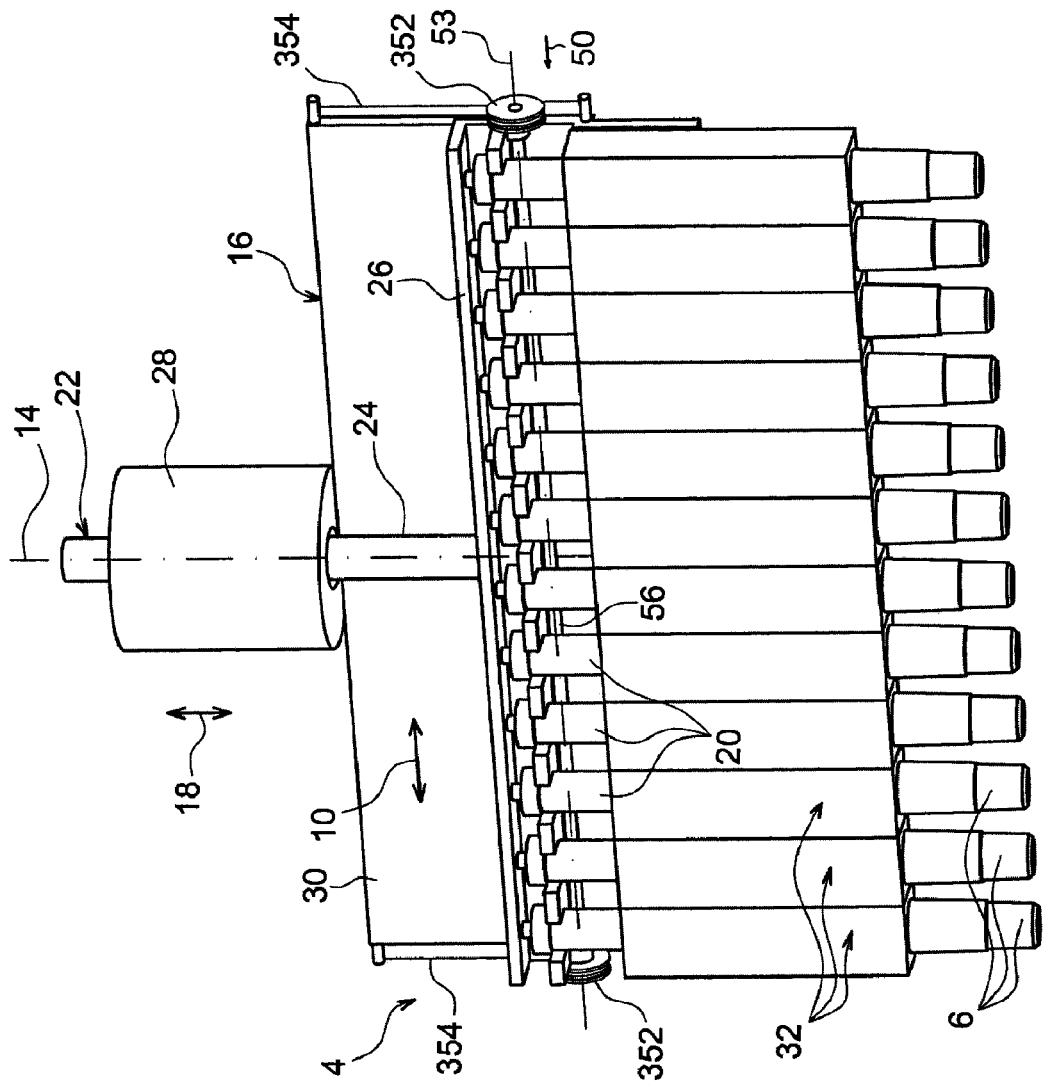
FIG. 7 shows a front, perspective view of a second bottom part of the multi-channel pipette of FIG. 1 including a fourth guidance assembly in accordance with an exemplary embodiment.

With reference to FIGS. 7 and 8, a fourth guidance assembly 50 of the multi-channel pipette of FIG. 1 is shown in accordance with an exemplary embodiment. The fourth guidance assembly 50 includes a third pulley 352, mating with a track formed by a wire 354 which is stretched and secured at its ends to fixed body 16, for example, on support structure 30, and wound one or more times around third pulley 352. Third pulley 352 may include a groove that receives the wire 354 running around it, with the winding around the pulley used to improve adhesion and to provide a slip-free running connection. Thus, the wire 354 extends from one of the two fixed ends toward third pulley 352 and extends in the groove around third pulley 352. The wire 354 may be wound around the groove one or more times in a helical manner and emerge from third pulley 352 in line with its first portion to extend up to the other end.

The described guidance assemblies can be enclosed by removable cover 40 without the need to modify the dimensions of removable cover 40 in relation to those provided for a conventional multi-channel pipette of the same size, but lacking the guidance assemblies.

The word "exemplary" is used herein to mean serving as an example, instance, or illustration. Any aspect or design described herein as "exemplary" is not necessarily to be construed as preferred or advantageous over other aspects or designs. Further, for the purposes of this disclosure and unless otherwise specified, "a" or "an" means "one or more". The exemplary embodiments may be implemented as a method, machine, or article of manufacture using standard programming and/or engineering techniques to produce software, firmware, hardware, and/or any combination thereof to control a device to implement the disclosed embodiments.

The foregoing description of exemplary embodiments of the invention have been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A device for use in a multi-channel pipetting system, the device comprising:
   a body;
   a plurality of modules mounted to the body, wherein each of the plurality of modules includes an orifice connecting to an intake chamber;
   a plurality of pistons mounted to a piston holder for simultaneous movement of the plurality of pistons in a first direction, wherein a piston of the plurality of pistons extends into the intake chamber of a module of the plurality of modules for movement in the first direction; and a guidance assembly comprising
a first rotating element;
a second rotating element;
a shaft connecting the first rotating element to the second rotating element, the shaft extending in a second direction, wherein the second direction is orthogonal to the first direction;
a first track extending parallel to the first direction; and
a second track extending parallel to the first direction, wherein the first rotating element is mounted to roll along the first track and the second rotating element is mounted to roll along the second track, wherein the first rotating element and the second rotating element are configured to roll simultaneously with movement of the plurality of pistons in the first direction.

2. The device of claim 1, wherein the first track and the second track are positioned on either side of a longitudinal central axis of the body.

3. The device of claim 2, wherein the first track and the second track are at the two ends of the piston holder in the second direction.

4. The device of claim 1, wherein the first track and the second track are mounted on the body and the shaft is mounted on the piston holder.

5. The device of claim 1, wherein the first track and the second track are mounted on the piston holder and the shaft is mounted on the body.

6. The device of claim 1, wherein the first rotating element and the second rotating element are mounted to rotate freely on the shaft.

7. The device of claim 1, wherein the first rotating element and the second rotating element are mounted rigidly to the shaft and the shaft is mounted to rotate freely on the piston holder.

8. The device of claim 1, wherein the first rotating element and the first track are formed of magnetic material such that a magnetic force maintains the first rotating element on the first track.

9. The device of claim 1, wherein the guidance assembly further comprises a first contact track and a second contact track, wherein a first end of the shaft contacts the first contact track, and further wherein a second end of the shaft contacts the second contact track to maintain the first rotating element on the first track and the second rotating element on the second track.

10. The device of claim 9, wherein the first rotating element is formed of an elastomer.

11. The device of claim 1, wherein the first rotating element comprises a toothed wheel and the first track comprises a rack that mates with the toothed wheel.

12. The device of claim 1, wherein the first rotating element comprises a toothed wheel and the first track comprises a chain that mates with the toothed wheel.

13. The device of claim 1, wherein the first rotating element comprises a pulley and the first track comprises a wire wound at least partially around the pulley.

14. The device of claim 13, wherein the pulley comprises a groove in which the wire is wound.

15. A multi-channel pipetting system comprising:
a first part; and
a second part, wherein, when the second part is mounted to the first part, the first part is configured to control movement of a guide rod, and further wherein the second part includes
a body;
a plurality of modules mounted to the body, wherein each of the plurality of modules includes an orifice connecting to an intake chamber;
a piston support head mounted to the guide rod;
a plurality of pistons mounted to the piston support head for simultaneous movement of the plurality of pistons in a first direction, wherein a piston of the plurality of pistons extends into the intake chamber of a module of the plurality of modules for movement in the first direction; and a guidance assembly comprising
a first rotating element;
a second rotating element;
a shaft connecting the first rotating element to the second rotating element, the shaft extending in a second direction, wherein the second direction is orthogonal to the first direction;
a first track extending parallel to the first direction; and
a second track extending parallel to the first direction, wherein the first rotating element is mounted to roll along the first track and the second rotating element is mounted to roll along the second track, wherein the first rotating element and the second rotating element are configured to roll simultaneously with movement of the plurality of pistons in the first direction.

16. The multi-channel pipetting system of claim 15, wherein the first rotating element and the first track are formed of magnetic material such that a magnetic force maintains the first rotating element on the first track.

17. The multi-channel pipetting system of claim 15, wherein the guidance assembly further comprises a first contact track and a second contact track, wherein a first end of the shaft contacts the first contact track, and further wherein a second end of the shaft contacts the second contact track to maintain the first rotating element on the first track and the second rotating element on the second track.

18. The multi-channel pipetting system of claim 15, wherein the first rotating element comprises a toothed wheel and the first track comprises a rack that mates with the toothed wheel.

19. The multi-channel pipetting system of claim 15, wherein the first rotating element comprises a toothed wheel and the first track comprises a chain that mates with the toothed wheel.

20. The multi-channel pipetting system of claim 15, wherein the first rotating element comprises a pulley and the first track comprises a wire wound at least partially around the pulley.

* * * * *

UNITED STATES PATENT AND TRADEMARK OFFICE
CERTIFICATE OF CORRECTION

| | | Page 1 of 1 |
|---|---|---|
| PATENT NO. | : 8,201,466 B2 | |
| APPLICATION NO. | : 12/206472 | |
| DATED | : June 19, 2012 | |
| INVENTOR(S) | : Roussel | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 758 days.

Signed and Sealed this
Twenty-eighth Day of August, 2012

David J. Kappos
*Director of the United States Patent and Trademark Office*